US00PP16733P3

(12) United States Plant Patent

Baker, Sr.

(10) Patent No.: US PP16,733 P3

(45) Date of Patent: Jun. 27, 2006

(54) SUGAR MAPLE TREE NAMED 'BAKHARL'

(50) Latin Name: *Acer saccharum*
Varietal Denomination: BAKharl

(75) Inventor: Robert W. Baker, Sr., Suffield, CT (US)

(73) Assignee: Baker West, Inc., Hubbard, OR (US)

( * ) Notice: Subject to any disclaimer, the term of this patent is extended or adjusted under 35 U.S.C. 154(b) by 0 days.

(21) Appl. No.: 10/880,257

(22) Filed: Jun. 28, 2004

(65) Prior Publication Data

US 2005/0289677 P1 Dec. 29, 2005

(51) Int. Cl.
*A01H 5/00* (2006.01)

(52) U.S. Cl. ..... Plt./224

(58) Field of Classification Search ..... Plt./224
See application file for complete search history.

*Primary Examiner*—Anne Marie Grunberg
(74) *Attorney, Agent, or Firm*—Klarquist Sparkman, LLP

(57) ABSTRACT

A sugar maple tree named 'BAKharl' having a brilliant and unique fall color presentation and an upright structure that develops into a full and spreading crown.

8 Drawing Sheets

Latin name of genus and species: *Acer saccharum.*
Variety denomination: 'BAKharl'.

BACKGROUND OF THE INVENTION

The present invention relates to a new and distinct variety of *Acer saccharum* that has been given the varietal name 'BAKharl'. *Acer saccharum* trees are indigenous to Connecticut, growing in parkways and lawns along the streets in the community of Suffield, Conn. and in the surrounding forest areas. I gathered *Acer saccharum* seeds from trees growing in parkways and lawns along the streets of Suffield, Conn., then planted and grew the seeds in seedbeds at my nursery in West Suffield, Conn. in 1980–82. From these nursery row plantings, the applicant tree was selected in 1993.

Although the parentage of this tree is unclear, it is definitely an *Acer saccharum* tree.

I was observing the *Acer* trees lined out and growing in the nursery rows, seeking one that displayed unusual and unique fall coloring and at the same time had an attractive shape and acceptable size for home and commercial landscape settings. The new tree was discovered and selected for its mixture of purple/burgundy, orange, and red leaves and moderate upright growth habit.

BRIEF SUMMARY OF THE INVENTION

As I observed the original tree of my new variety, the uniqueness of this tree became apparent because of its brilliant and unique fall color presentation. In particular, the leaf color starts changing earlier in the fall than most *Acer saccharum* varieties, and changes from its deep summer green to a mix of colors: purple-reds (like a burgundy), deep reds, orange, and yellow-greens. Leaves become a color mix from all greens turning to mix of these colors. As the fall weeks progress, leaf colors maintain their mix until finishing out to predominately dark reds. The new tree holds leaves and color well into fall. In addition, my new variety was selected for its upright structure that develops into a full and spreading crown. As a young tree, it exhibits a moderate upright habit. This moderate upright growth habit becomes rounded and spreading at the crown. This combination of characteristics distinguish my new tree from other *Acer saccharum* of which I am aware.

My new variety was asexually propagated by beginning budding in 1996 at my direction, in Hubbard, Oreg. as follows. Bud wood was taken from the discovered tree growing in Connecticut and budded on to one to two year old *Acer saccharum* under stock seedling trees growing in the field rows at a nursery in Hubbard, Oreg. The asexually propagated trees are true to type.

The seed that grew into this variety was planted with other seeds in a nursery seedbed at a nursery in West Suffield, Conn. The resulting trees, including the tree of my new variety, were transplanted to nursery rows four years later. In 1993, I selected the tree of my new variety. The original tree of my variety is now about 22 years old and demonstrates very good resistance to disease, frost/freezing, and heat. The asexually propagated trees of my new variety exhibit this same hardiness.

The seed and pollen parent trees that produced the seeds that were planted at the nursery cannot be identified as they came from among a group of trees growing in the community. However, the new variety displays a mixture of fall red/burgundy, yellow/green, and red leaf color that has not been observed in any of the trees in the community. The earliest asexually reproduced trees are now about seven years old.

BRIEF DESCRIPTION OF THE DRAWINGS

The accompanying photographs depict the color of the tree and foliage of my new variety as nearly true as is reasonably possible to make the same in a color illustration of this character.

DETAILED BOTANICAL DESCRIPTION

Figure 1:
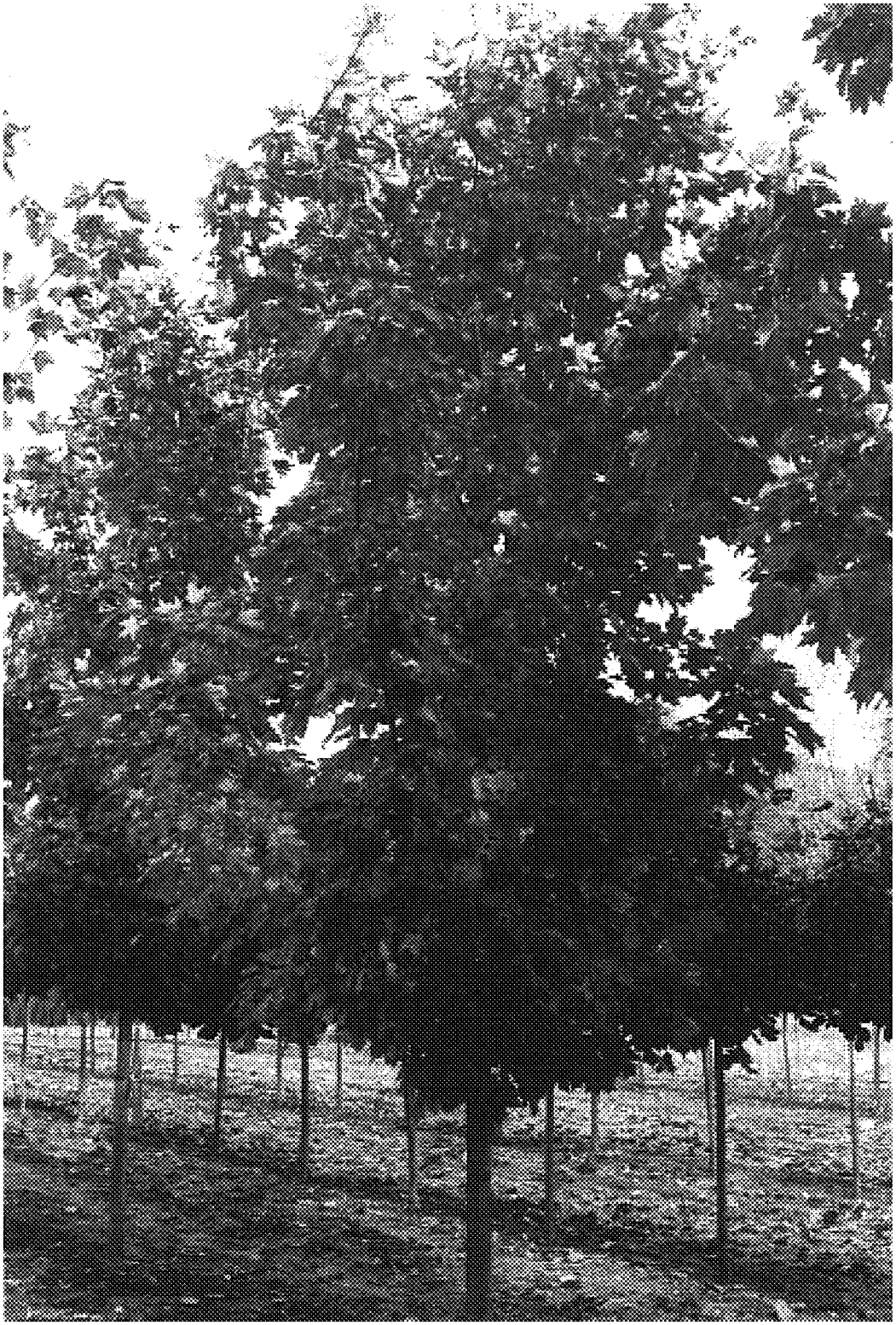
FIG. 1 is a photograph of a seven-year-old asexually reproduced tree of my new variety showing the moderate upright growing habit of these trees at this age.
Figure 2:
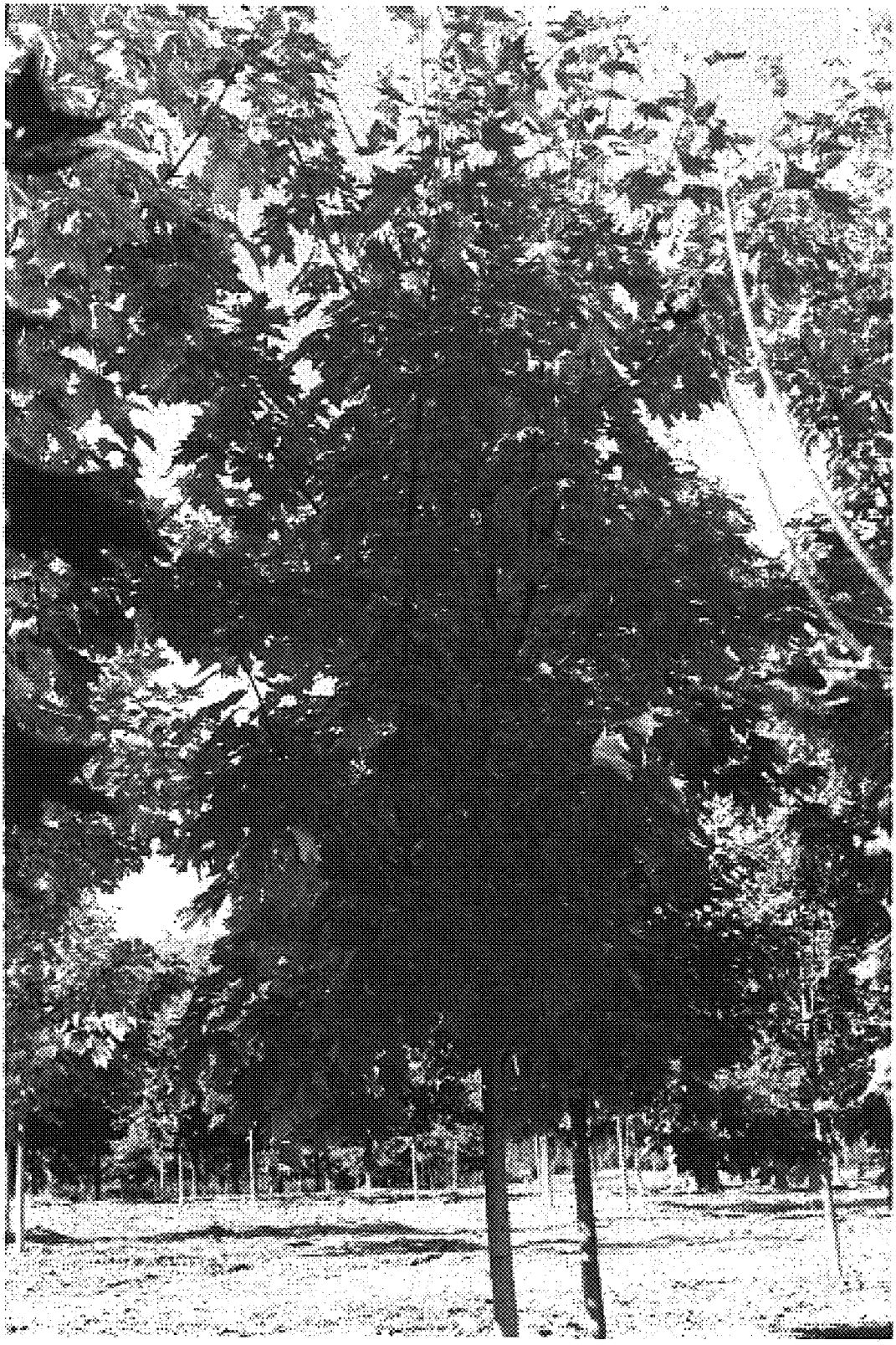
FIG. 2 is a photograph of a six-year-old asexually propagated tree of my new variety at mid-season with red leaf colors.
Figure 3:
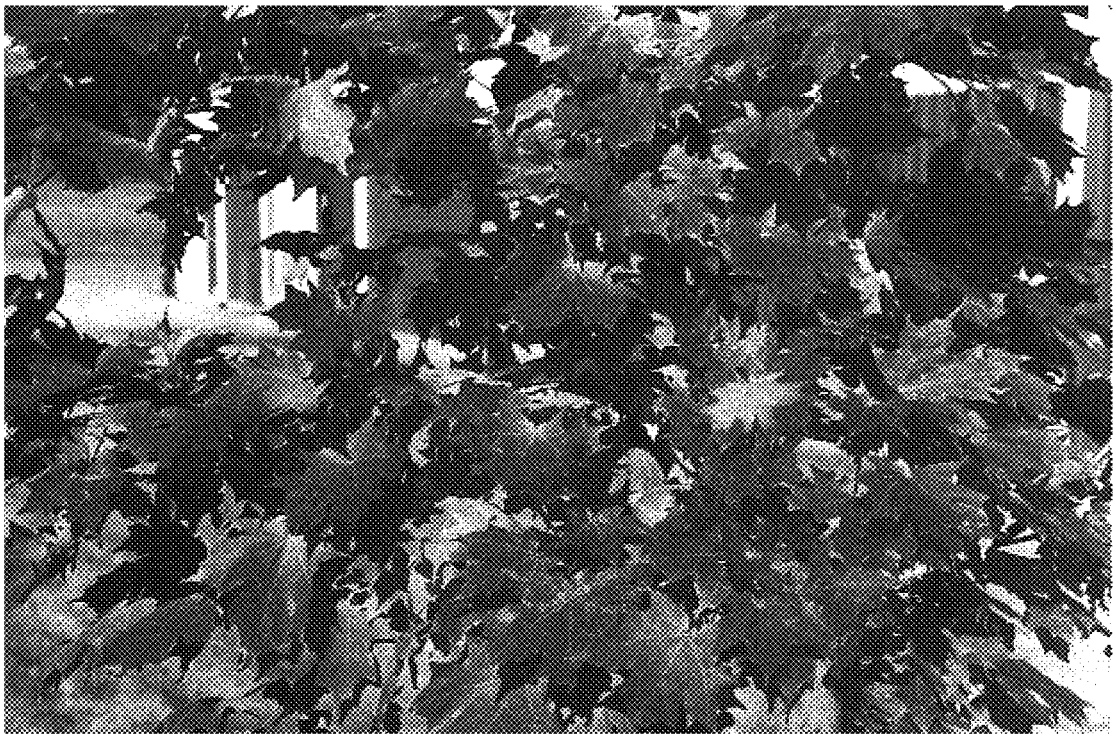
FIG. 3 is a photograph of a tree of my new variety with orange-red leaf color and showing leaf growing habit.
Figure 4:
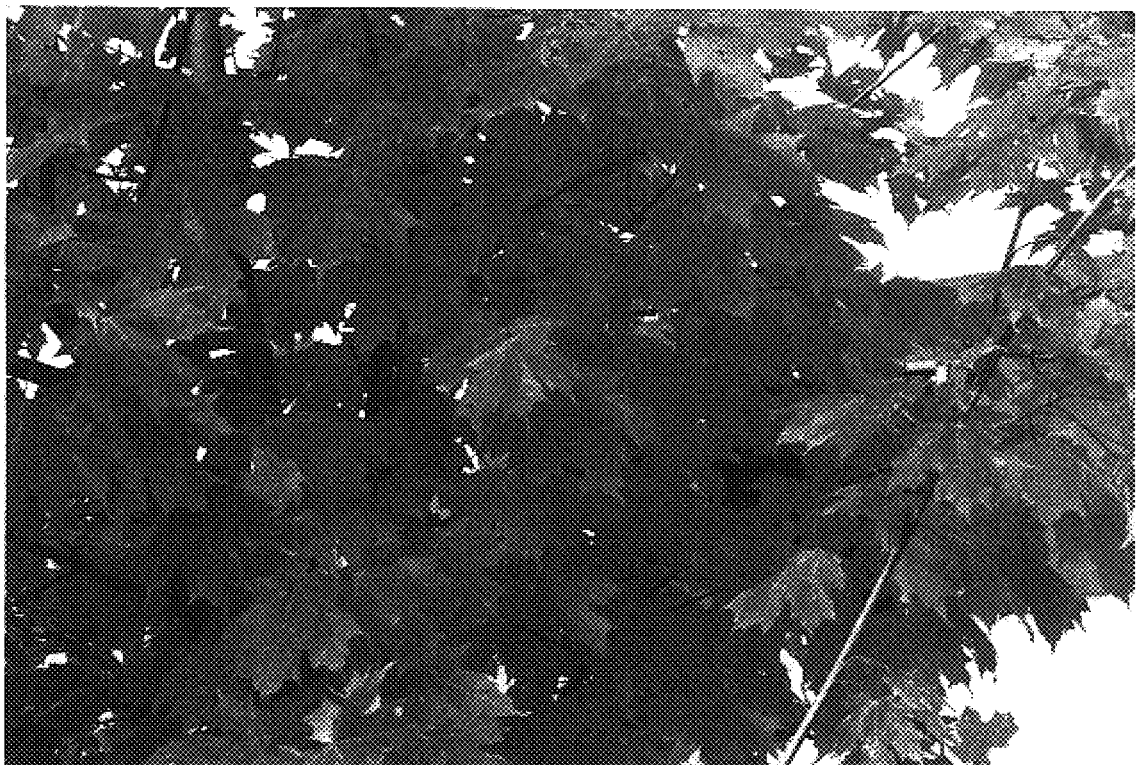
FIG. 4 is a photograph of a tree of my new variety showing red leaf color and leaf growing habit.
Figure 5:
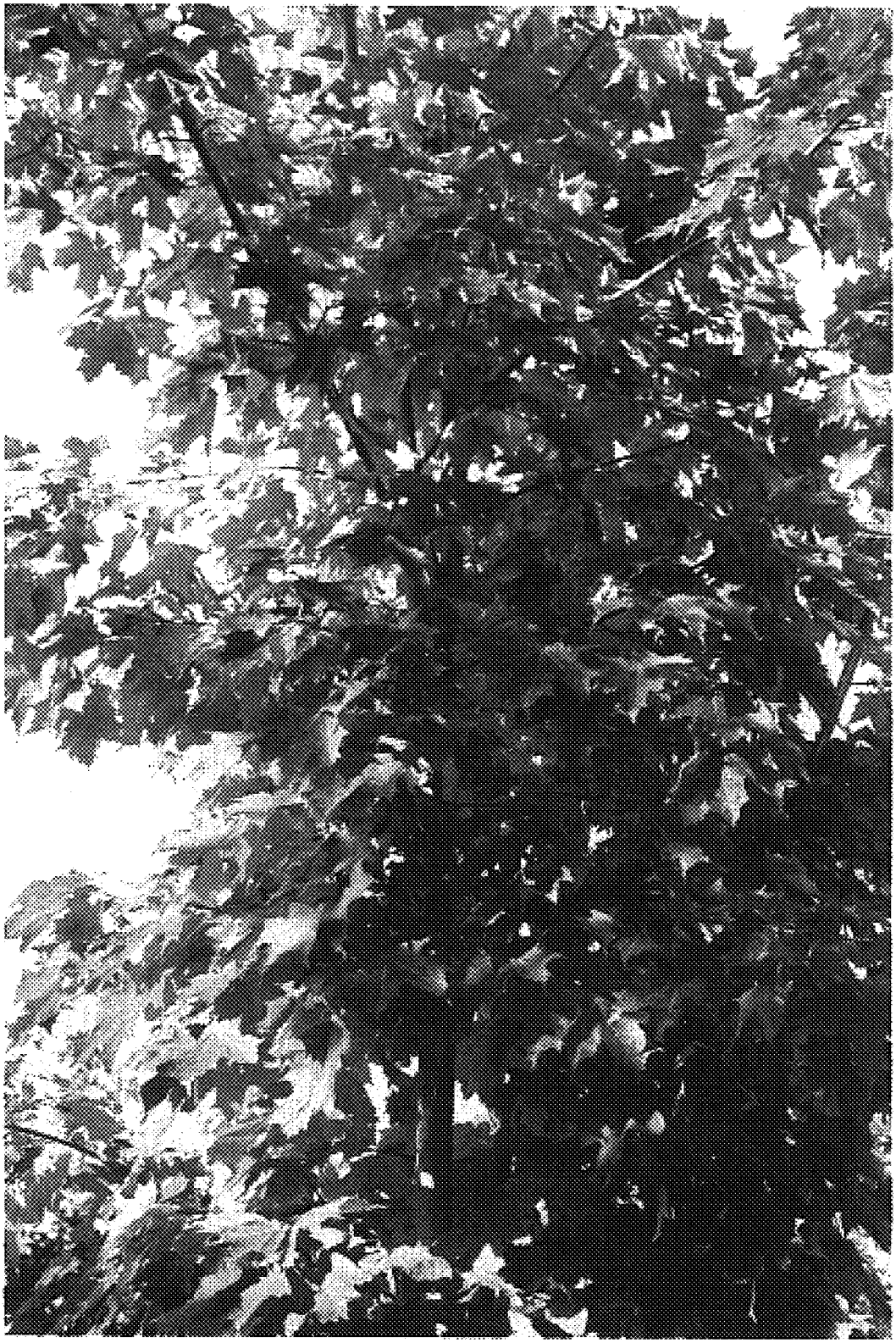
FIG. 5 is a photograph of a tree of my new variety showing burgundy-red leaf color.
Figure 6:
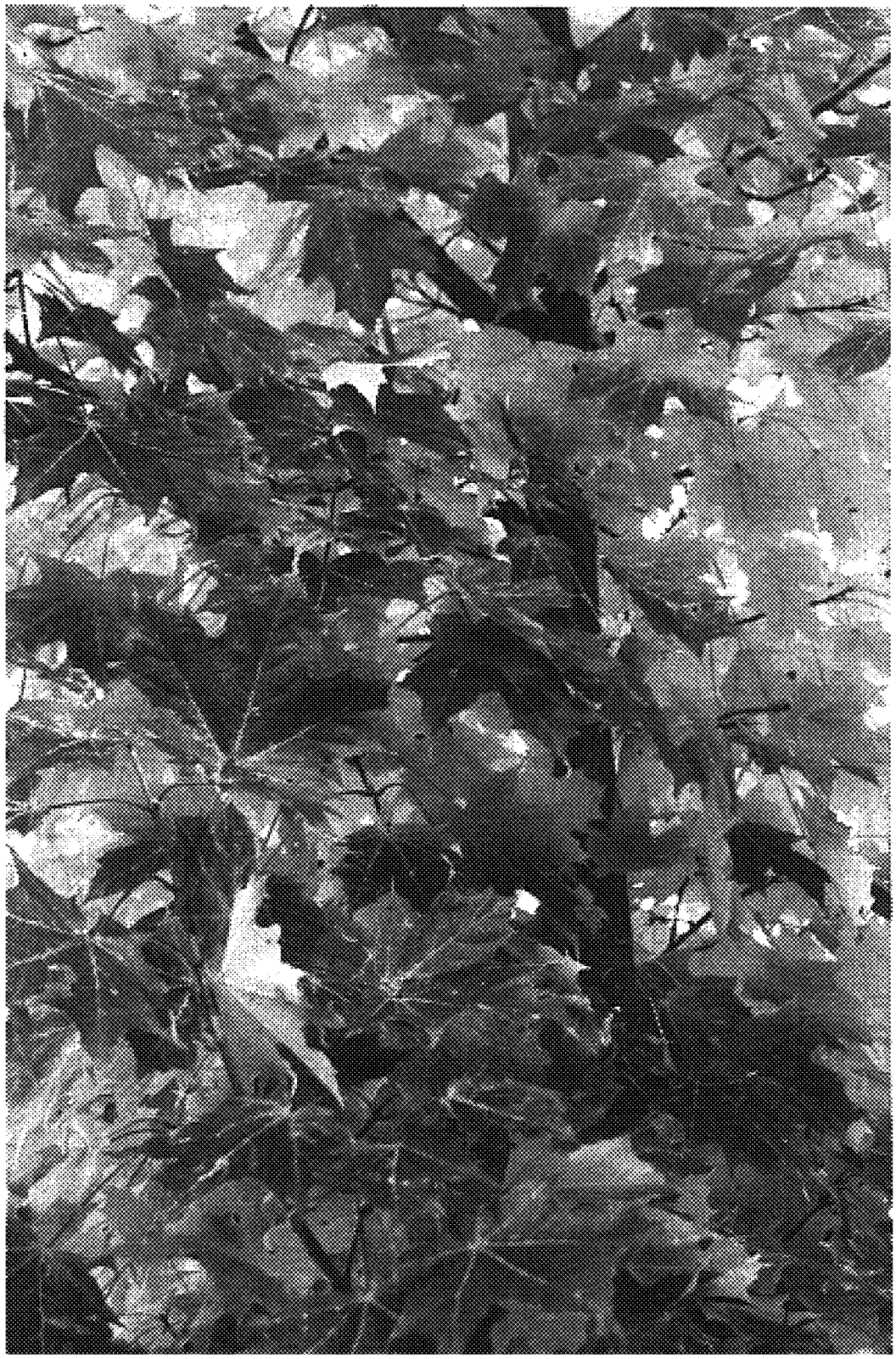
FIG. 6 is a photograph of a tree of my new variety showing burgundy leaf color.
Figure 7:
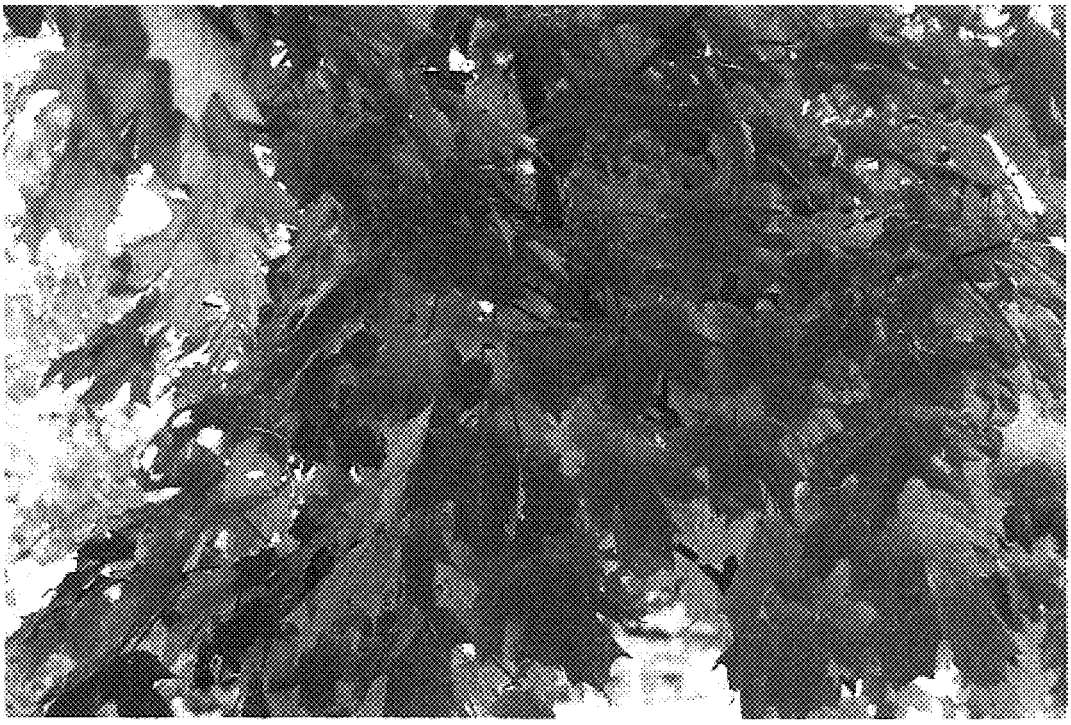
FIG. 7 is a photograph of a tree of my new variety showing an exemplary leaf color mix.
Figure 8:
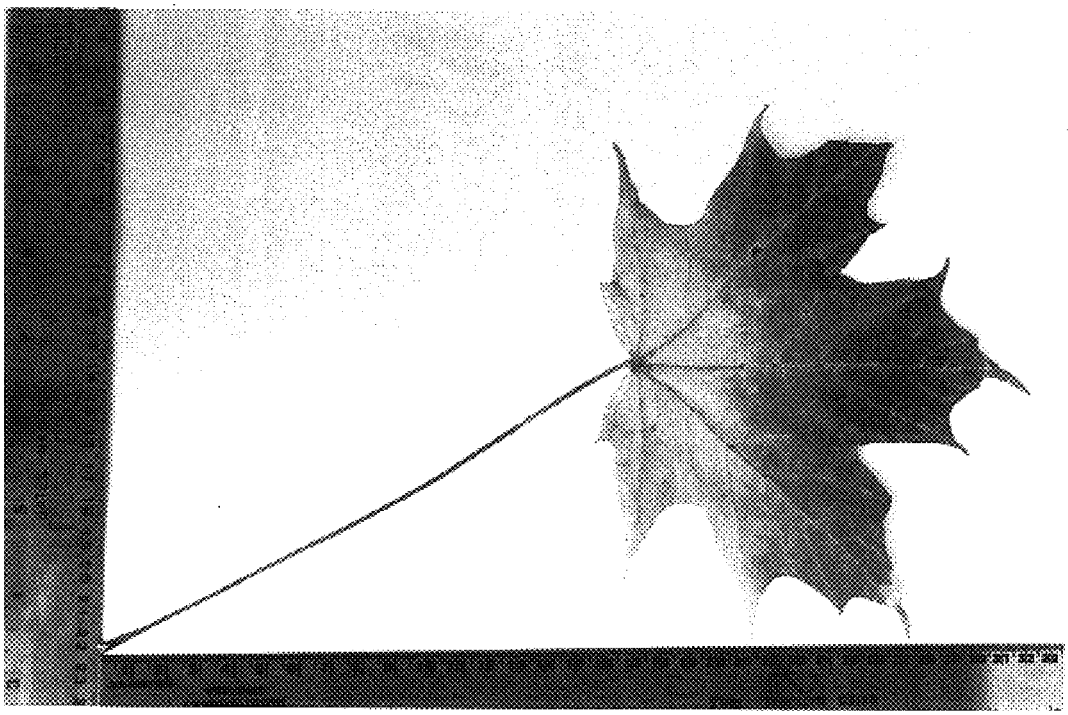
FIG. 8 is a photograph of a typical leaf structure and size of a leaf of my new variety.

My 'BAKharl' variety of *Acer saccharum* is currently growing in a nursery near West Suffield, Conn. Asexually reproduced trees were grown in nursery fields for two years at a nursery in Hubbard, Oreg. They were dug in February 1998 and transported (Feb. 26th) to a nursery West Suffield, Conn. and planted directly into an open nursery field in rows.

My new tree has not been observed under all growing conditions, and thus, variations may occur as a result of different growing conditions. The following is a detailed description of my new variety of tree with color terminology in accordance with The Royal Horticultural Society (R.H.S.) Colour Chart published by The Royal Horticultural Society in London. The observations are of the original tree and of six to seven year old asexually propagated trees of my new variety growing in a nursery in West Suffield, Conn.

Trees of my new variety, both the older and younger specimens, have been through seasons of drought and high moisture (spring and summer) along with very cold hard winters. They have survived all these environmental conditions and maintained a high level of growing vigor and disease and insect resistance. In the first six years, trees of my new variety have grown on average of about 36 inches per year growth.

Parentage: Unknown. Seeds from *Acer saccharum* trees were collected and planted in seedbeds at a nursery in West Suffield, Conn. in 1980–82. From these nursery row plantings, the original tree of my new variety was selected in 1993. My new variety of tree was discovered and selected for its mixture of purple/burgundy, orange and red leaves and moderate upright growth habit.

Tree shape: Habit is upright forming a tight rounded to oval head pattern. Ascending branches. Head and foliage was moderately dense during drought, but full and dense in all other years. Young tree has irregular crown. Older tree has a fuller, crown that is spreading.

Trunk: At about age seven, the asexually reproduced trees of my new variety had a typical diameter of about three inches measured twelve inches above the ground.

Bark: At seven years, the bark is grey-brown (RHS 199B). Smooth, except for thin, broken vertical fissuring. The bark of the 22 year old original tree has taken on the deeply furrowed texture characteristic of *Acer saccharum*.

Branching habit: Branches are upright, ascending, forming a columnar head in young trees. As the tree matures, the crown becomes more oval and more spreading. 18 degree angle from the trunk at emergence. Becoming 35 to 49 degrees as branches become elongated. Side branches arising from leader at 40 to 60 degree angle. One year old branch is grey-brown, (RHS 199D) with slight coarseness. Three year old branches are grey-brown, (RHS 199B). Branches develop vertical fissures with small scaling which gives a course texture.

Branch lenticels: Straight, narrow, running vertical. Length is 1 mm. Very dense. Yellow-white color (RHS 158A).

Branch internodes: Average=10 cm at seven years. Becoming 14 cm at 22 years.

Leaf number and arrangement: Opposite, simple.

Foliage:

*Leaf size* (*sampling of typical leaves*).—Leaf (including petiole): 30 cm length average (range 28 cm to 31.5 cm) 20.5 cm wide average.

*Petiole.*—16 cm average (range 13 cm to 20.5 cm). Yellow-green, (RHS 154C) to fall's red-orange (RHS 30A).

*Leaf shape.*—Overall Shape: Opposite — simple leaf. Incised margins. No serration. Three to five lobed, cordate. Base: Truncate to cordate. Apex: Pointed, acute to acuminate. Margin: Incised. Leaf color in summer: Upperside: Green (RHS 141A). Underside: Green (RHS 130D). Leaf color in fall: Mixture of colors. Leaves progressively change from red-purple to red to yellow-orange or orange-red with individual leaves progressing through different color shades. Examples of typical fall color leaf changes are as follows: First color change: Red-purple (RHS 60B); Mid-fall color: red (RHS 46A); Late fall color (finish): yellow orange (RHS 21B). First color change: Red-purple (RHS 59C); Mid-fall color: red (RHS 44A); Late fall color (finish): orange red (RHS 34A). First color change: Red-purple (RHS 59A); Mid-fall color: red (RHS 41A); Late fall color (finish): orange red (RHS 34A). Vein size: Palmate, 1 mm, yellow-green (RHS 154C). Texture: Glabrous upperside and underside.

Stipules: None.

Pest and disease resistance: My new tree variety appears to be tolerant to disease, insects and drought.

Winter hardiness: Grown and observed in West Suffield, Conn. and Hubbard, Oreg. (USDA Zones 4b (−20° F. to −25° F.) to 8 (10° F. to 20° F.).

I claim:

1. A new and distinct variety of sugar maple tree substantially as herein shown and described, characterized particularly as to novelty by its brilliant and unique fall color presentation and its upright structure that develops into a full and spreading crown.

* * * * *